United States Patent
Larkin et al.

(10) Patent No.: US 12,114,936 B2
(45) Date of Patent: Oct. 15, 2024

(54) SHAPE SENSOR SYSTEMS WITH REDUNDANT SENSING

(71) Applicant: INTUITIVE SURGICAL OPERATIONS, INC., Sunnyvale, CA (US)

(72) Inventors: David Q. Larkin, Menlo Park, CA (US); Vincent Duindam, San Francisco, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 6 days.

(21) Appl. No.: 17/576,696

(22) Filed: Jan. 14, 2022

(65) Prior Publication Data

US 2022/0133414 A1    May 5, 2022

Related U.S. Application Data

(63) Continuation of application No. 14/908,386, filed as application No. PCT/US2014/048175 on Jul. 25, 2014, now Pat. No. 11,266,466.
(Continued)

(51) Int. Cl.
*A61B 34/20* (2016.01)
*A61B 5/06* (2006.01)
*A61B 90/00* (2016.01)

(52) U.S. Cl.
CPC .............. *A61B 34/20* (2016.02); *A61B 5/065* (2013.01); *A61B 2034/2061* (2016.02); *A61B 2090/0818* (2016.02)

(58) Field of Classification Search
None
See application file for complete search history.

(56) References Cited

U.S. PATENT DOCUMENTS

| | | | |
|---|---|---|---|
| 6,389,187 B1 | 5/2002 | Greenaway et al. | |
| 7,520,176 B1 | 4/2009 | Ko et al. | |

(Continued)

FOREIGN PATENT DOCUMENTS

| | | | |
|---|---|---|---|
| JP | 2009530069 A | 8/2009 | |
| JP | 2011200341 A | 10/2011 | |

(Continued)

OTHER PUBLICATIONS

Extended European Search Report for Application No. 14832981.6, mailed on Jun. 6, 2017, 9 pages.
(Continued)

*Primary Examiner* — Shahdeep Mohammed
(74) *Attorney, Agent, or Firm* — Haynes & Boone, LLP.

(57) ABSTRACT

A method of operating a shape sensing apparatus comprises receiving shape data from a first shape sensor. The first shape sensor includes a first plurality of optical cores extending between a first section and a second section of an elongated optical fiber. The method further comprises receiving shape data from a second shape sensor. The second shape sensor includes a second plurality of optical cores extending between the first and second sections of the elongated optical fiber. The method further comprises determining a shape of the elongated optical fiber between the first and second sections by combining the shape data from the first and second shape sensors.

20 Claims, 12 Drawing Sheets

Related U.S. Application Data

(60) Provisional application No. 61/859,648, filed on Jul. 29, 2013.

(56) References Cited

U.S. PATENT DOCUMENTS

| | | |
|---|---|---|
| 7,715,994 B1 | 5/2010 | Richards et al. |
| 7,772,541 B2 | 8/2010 | Froggatt et al. |
| 7,930,065 B2 | 4/2011 | Larkin et al. |
| 2006/0013523 A1 | 1/2006 | Childers et al. |
| 2007/0065077 A1 | 3/2007 | Childers et al. |
| 2007/0123748 A1 | 5/2007 | Meglan |
| 2009/0088634 A1 | 4/2009 | Zhao et al. |
| 2009/0123111 A1 | 5/2009 | Udd |
| 2009/0314925 A1 | 12/2009 | Van et al. |
| 2009/0324161 A1* | 12/2009 | Prisco ............... G01L 1/246 |
| | | 385/12 |
| 2010/0215311 A1 | 8/2010 | Moore |
| 2011/0071508 A1 | 3/2011 | Duval et al. |
| 2011/0090486 A1 | 4/2011 | Udd |
| 2011/0109898 A1* | 5/2011 | Froggatt ............. G01M 11/31 |
| | | 356/73.1 |
| 2011/0113852 A1 | 5/2011 | Prisco |
| 2011/0176776 A1* | 7/2011 | Imamura ........... G02B 6/02042 |
| | | 385/59 |
| 2011/0202069 A1 | 8/2011 | Prisco et al. |
| 2011/0222828 A1* | 9/2011 | Sasaoka ............ G02B 6/02042 |
| | | 385/127 |
| 2011/0224825 A1 | 9/2011 | Larkin et al. |
| 2012/0197097 A1* | 8/2012 | Chan ..................... A61B 90/06 |
| | | 600/478 |
| 2012/0289777 A1 | 11/2012 | Chopra et al. |
| 2013/0085333 A1 | 4/2013 | Ramamurthy et al. |
| 2013/0345719 A1 | 12/2013 | Donhowe et al. |
| 2014/0275997 A1 | 9/2014 | Chopra et al. |
| 2016/0102969 A1 | 4/2016 | Verstege et al. |
| 2016/0157939 A1 | 6/2016 | Larkin et al. |

FOREIGN PATENT DOCUMENTS

| | | |
|---|---|---|
| JP | 2013508058 A | 3/2013 |
| WO | WO-2008093517 A1 | 8/2008 |
| WO | WO-2010111090 A1 | 9/2010 |
| WO | WO-2011100124 A1 | 8/2011 |
| WO | WO-2012168855 A1 | 12/2012 |

OTHER PUBLICATIONS

International Search Report and Written Opinion for Application No. PCT/US2014/048175, mailed on Nov. 5, 2014, 16 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

SHAPE SENSOR SYSTEMS WITH REDUNDANT SENSING

CROSS-REFERENCE TO RELATED APPLICATIONS

This application is a continuation of U.S. patent application Ser. No. 14/908,386, filed Jan. 28, 2016, which is the U.S. National Phase of International Application No. PCT/US2014/048175, filed Jul. 25, 2014, which claims priority to and the benefit of U.S. Provisional Application No. 61/859,648, entitled "SHAPE SENSOR SYSTEMS WITH REDUNDANT SENSING," filed Jul. 29, 2013, all of which are incorporated by reference herein in their entireties.

FIELD

The present disclosure is directed to systems and methods for using shape sensor systems to track anatomical targets and/or interventional instruments, and more particularly to systems and methods using redundant shape sensors to improve the accuracy of shape sensor systems.

BACKGROUND

Minimally invasive medical techniques are intended to reduce the amount of tissue that is damaged during interventional procedures, thereby reducing patient recovery time, discomfort, and deleterious side effects. To track the location of anatomical targets, implanted devices, and/or interventional instruments (including surgical, diagnostic, therapeutic, or biopsy instruments) within a patient anatomy, minimally invasive sensor systems may be used. In existing systems, electro-magnetic (EM) navigation may be used to track the movement of interventional instruments, implanted devices, or targets in a patient anatomy. Although EM navigation systems are useful for many procedures, they may be subject to magnetic interference from other equipment in the surgical suite. For example, a C-arm of a fluoroscopic imaging system or metal instruments may generate magnetic interference with EM navigation systems, causing unacceptable errors in the tracking of an interventional instrument. In other existing systems, optical fiber shape sensor systems may be used to track the movement of interventional instruments in a patient anatomy. Optical fiber shape sensor systems monitor the strain at various points along a single optical fiber to determine the shape of optical fiber. From the shape of the single optical fiber, the pose (position and orientation) of the various points along the optical fiber can be derived. The error associated with the derived poses for the various points along the single optical fiber may increase with distance from the optical fiber interrogator due to error accumulation. Improved navigation systems and methods are needed for tracking interventional instruments, implanted devices, and anatomic targets in surgical environments.

SUMMARY

The embodiments of the invention are summarized by the claims that follow the description.

In one embodiment, a method of operating a shape sensing apparatus comprising receiving first shape data from a first shape sensor section including a first elongated optical fiber extending between a first location and a second location. The method further comprises receiving second shape data from a second shape sensor section including a second elongated optical fiber extending between a third location and a fourth location. The method further comprises determining a position of an end portion of the first shape sensor section using the second shape data from the second shape sensor section.

In another embodiment, a method of operating a shape sensing apparatus comprises receiving shape data from a first shape sensor. The first shape sensor includes a first plurality of optical cores extending between a first section and a second section of an elongated optical fiber. The method also includes receiving shape data from a second shape sensor. The second shape sensor including a second plurality of optical cores extending between the first and second sections of the elongated optical fiber. The method further includes determining a shape of the elongated optical fiber between the first and second sections by combining the shape data from the first and second shape sensors.

In another embodiment, a method of operating a shape sensing apparatus comprises receiving first shape data from a first shape sensor having a first portion coupled to a reference fixture and a second portion coupled to a first anatomic target. The method also includes receiving second shape data from a second shape sensor having a first portion coupled to the reference fixture and a second portion coupled to the first anatomic target. The first portions of the first and second shape sensors are maintained in a fixed kinematic relationship, and the second portions of the first and second shape sensors are maintained in a fixed kinematic relationship. The method also includes determining a position of the second portion of the first shape sensor section using the second shape data from the second shape sensor.

In another embodiment, a method of operating a shape sensing apparatus comprises receiving shape data from an elongated shape sensor having a first portion coupled to a reference fixture, a second portion coupled to an anatomic target, and a third portion coupled to the reference fixture. The first and third portions are maintained in a fixed kinematic relationship. The method further comprises determining a first shape of the elongated shape sensor between the first and second portions, determining a second shape of the elongated shape sensor between the third and second portions, and determining a position of the second portion at the anatomic target from the first and second shapes.

In another embodiment, a system comprises non-transitory computer readable media containing computer executable instructions for operating a shape sensing apparatus. The instructions include instructions for receiving shape data from a first shape sensor. The first shape sensor includes a first plurality of optical cores extending between a first section and a second section of an elongated optical fiber. The instructions also include instructions for receiving shape data from a second shape sensor. The second shape sensor includes a second plurality of optical cores extending between the first and second sections of the elongated optical fiber. The instructions also include instructions for determining a shape of the elongated optical fiber between the first and second sections by combining the shape data from the first and second shape sensors.

Additional aspects, features, and advantages of the present disclosure will become apparent from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

Figure 12:
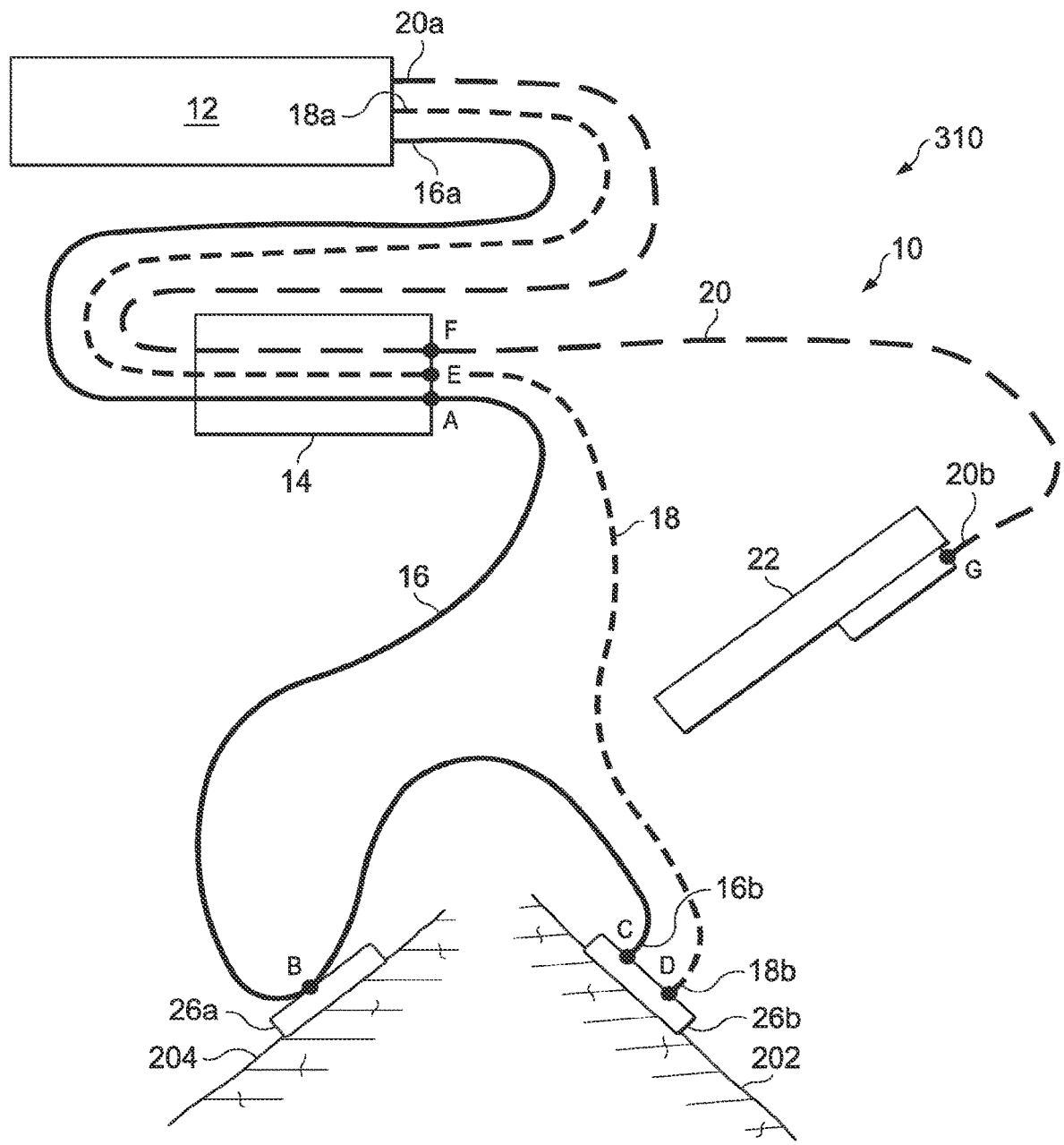
FIG. 12 is a sensor system with a plurality of optical fiber sensors and an interventional instrument in accordance with another embodiment of the present disclosure.
Figure 13:
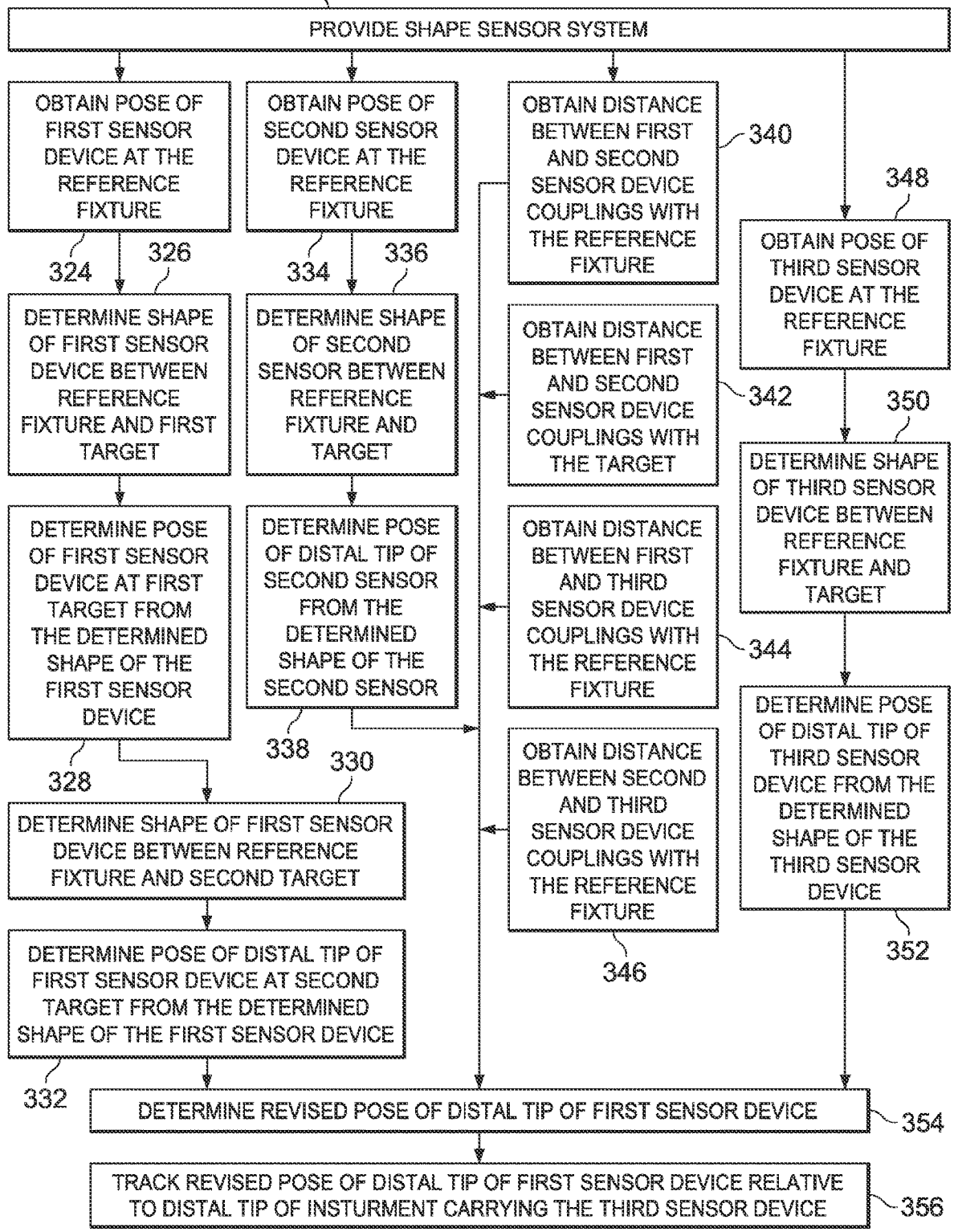

FIG. 13 a method of using the sensor system of FIG. 12.

Figure 14:
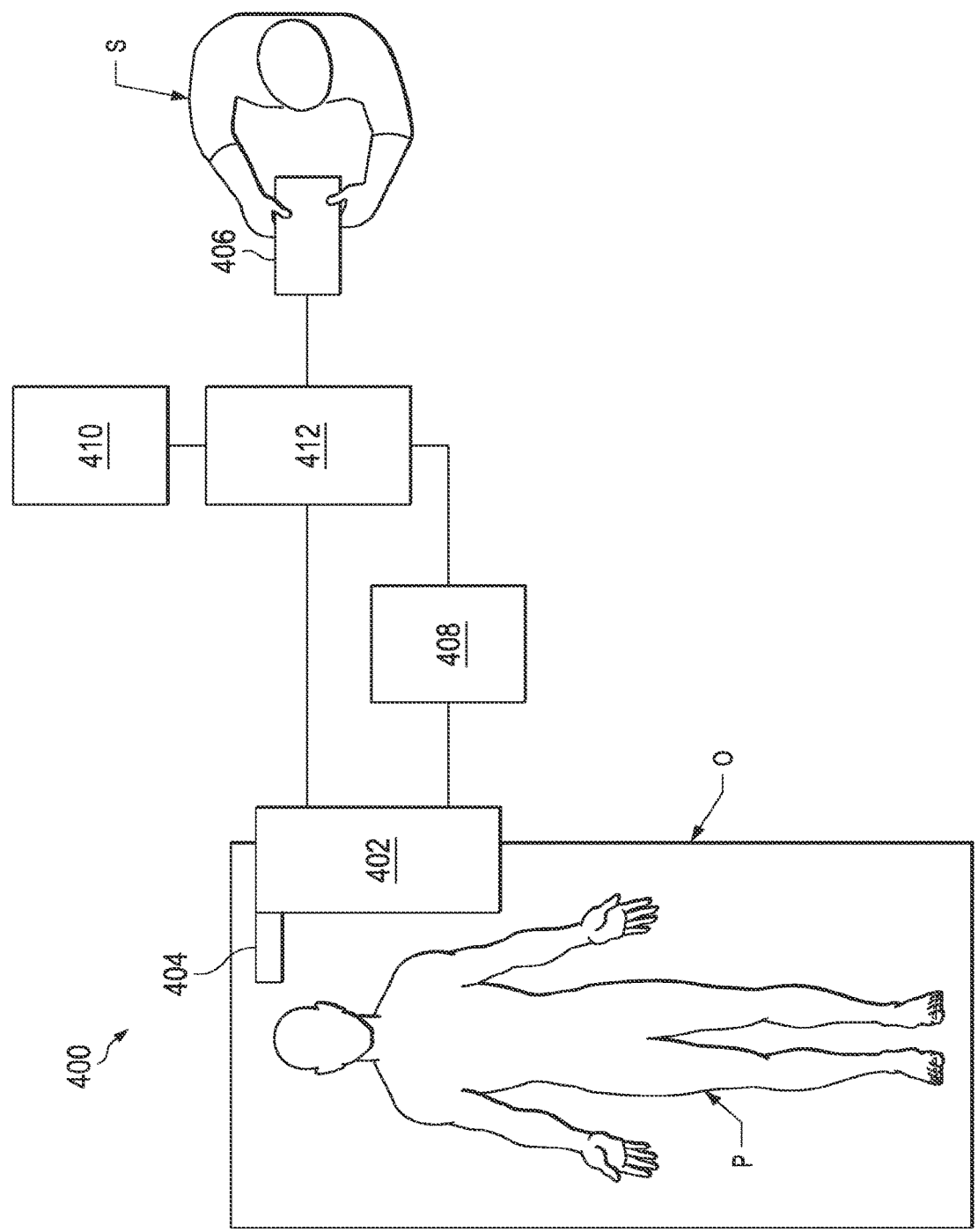

FIG. 14 is a robotic interventional system, in accordance with an embodiment of the present disclosure.

DETAILED DESCRIPTION

In the following detailed description of the aspects of the invention, numerous specific details are set forth in order to provide a thorough understanding of the disclosed embodiments. However, it twill be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various devices and portions of devices in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom), As used herein, the term "shape" refers to a set of poses, positions, or orientations measured along an elongated object.

Figure 1:
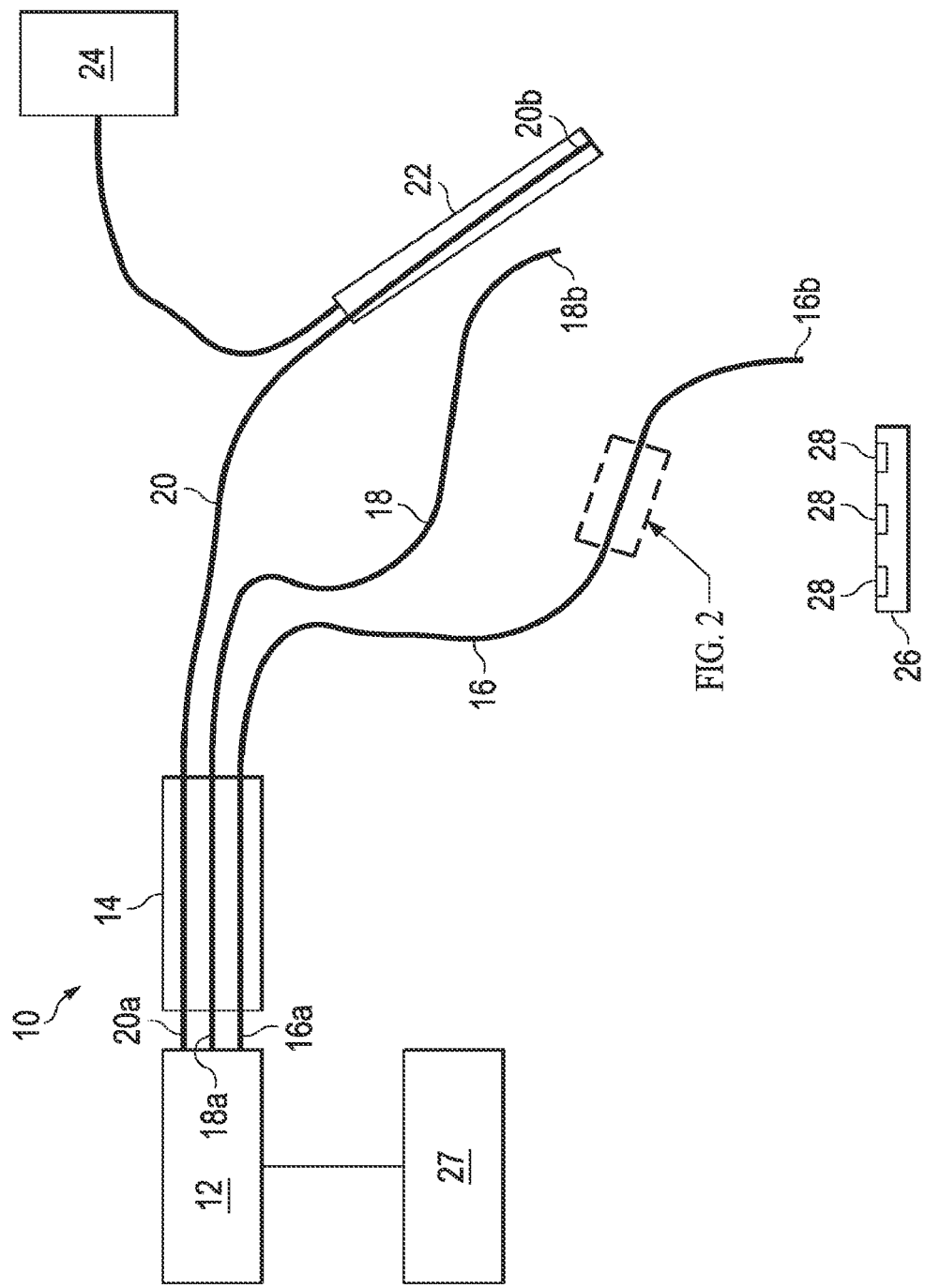
FIG. 1 is a sensor system in accordance with an embodiment of the present disclosure.

Referring to FIG. 1, a sensor system for use in, for example, surgical, diagnostic, therapeutic, biopsy, medical monitoring, or medical evaluation is generally indicated by the reference numeral 10, The sensor system 10 generally includes an Interrogation system 12; a reference fixture 14; sensor devices 16, 18, 20; an interventional instrument 22; a control system 24; a target fixture 26; and a sensor processing and control system 27. In various embodiments, one or more of these components of the sensor system may be omitted or multiple components of the same type may be included. As will be described in detail below, the sensor system 10 includes redundant sensor components which may increase the accuracy of the shape sensing and pose determination functions of the system. The redundant sensor components may also identify the sources and locations of sensor inaccuracies, for example in regions with tight bends, high tensions, or significant twisting, and correct for those inaccuracies.

The interrogation system 12 generates light and detects returning light to determine the current shape of the sensor devices 16, 18, 20. The interrogation system 12 may also process the returned data for display to the clinician. This information, in turn, in can be used to determine other related variables, such as pose, velocity and acceleration of the targets or instruments to which the sensor devices are connected. The sensor devices 16, 18 are coupled at proximal ends 16a, 18a, respectively, to the interrogation system 12. The sensor devices 16, 18 also have distal ends 16h, 18b, respectively. The sensor device 20 is coupled at a proximal end 20a to the interrogation system 12 and at a distal end 20b to the interventional instrument Although the sensor device 20 is shown extending entirely within or along the interventional instrument, in various alternative embodiments, the sensor device may extend only partially within or along the interventional instrument. The intervention instrument 22 is coupled to a manual or remotely operated control system 24.

Each of the sensor devices 16, 18, 20 is coupled to the reference fixture 14 at an intermediate portion along its length between the proximal and distal ends. The poses of the coupled portions of the sensor devices 16, 18, 20 are held fixed by the reference fixture 14. Further, the poses of the coupled portions of the sensor devices 16, 18, 20 are maintained in known kinematic relationships with respect to each other by the reference fixture 14. For example, the relationships between sensors and fixtures may be fixed, such as where the sensor device does not move with any degree of freedom relative to the reference fixture. Alternatively, the relationships between sensors and fixtures may be movable but known, such as where a sensor is movable relative to the reference fixture within a known range. For example, a reference fixture may have a rotating joint with a known rotation angle, but the relative position of the sensors to each other and to the reference fixture is still known. The reference fixture 14 may be, for example, formed of a rigid metal, polymer, or ceramic material and may include grooves, tubes, clamps, and/or other mechanical connectors that receive a portion of the sensor device and maintain it in a fixed relationship with respect to the fixture and with respect to the other coupled sensor devices. In one example, the reference fixture may be formed of an aluminum plate with several machined, tight-fitting parallel grooves to which the sensor devices may be glued or otherwise affixed. The position and orientation offsets between the coupled sensor devices are thus known at the location at which the sensor devices are coupled to the reference fixture 14.

In use, the target fixture 26 is anchored to an anatomical structure of a patient anatomy. The target fixture 26 includes connectors 28 for fixing a portion of one or more sensor devices 16, 18 to the target fixture and maintaining the fixed portions of the sensor devices in a predefined shape or pose. The sensor devices may be glued, mechanically held, otherwise affixed within the target fixture. In one example, the target fixture may be a small aluminum plate with a plurality of tight-fitting grooves in which portions of the sensor devices are maintained in fixed kinematic relationships.

Figure 2:
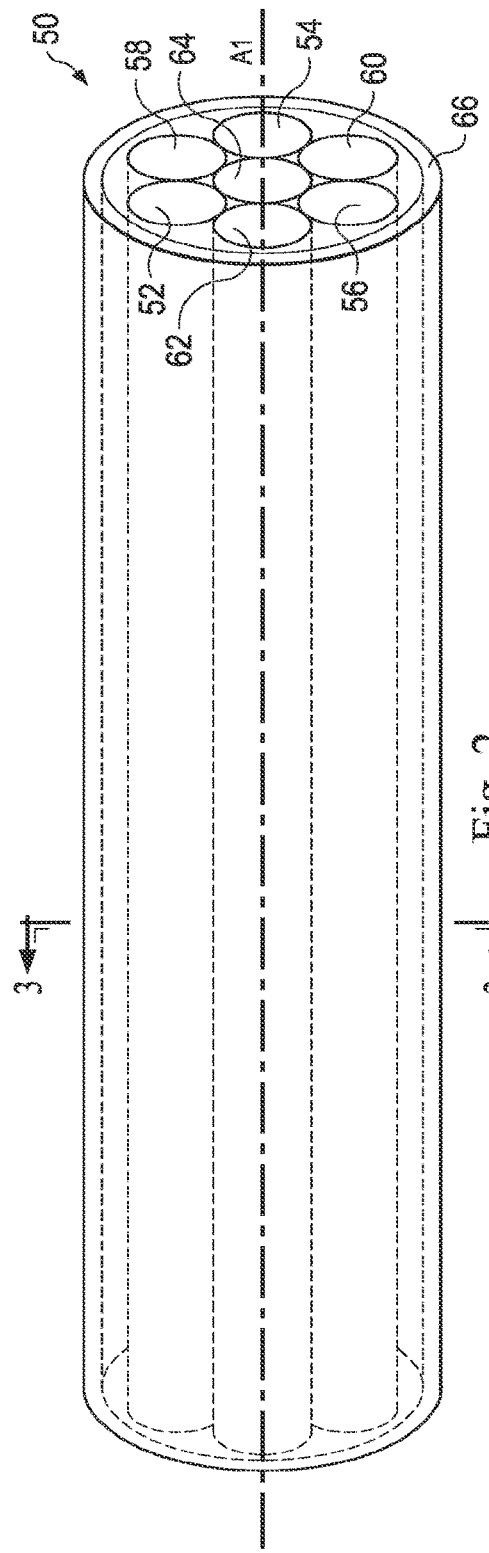
FIG. 2 is a multi-core optical fiber component of the sensor system of FIG. 1.

As shown in FIG. 2, the sensor device 16 includes a multicore optical fiber 50 including seven cores 52, 54, 56, 58, 60, 62, 64 within a cladding 66. In one embodiment, the multi-core optical fiber has a diameter of approximately 200 μm. In other embodiments, the dimensions may be larger or smaller. Sensor devices 18 and 20 may have a similar construction and so will not be described in further detail. In alternative embodiments, the sensor device may have more or fewer than seven cores. Alternatively, the sensor device may include multiple optical fibers, each with one or more optical curers.

Each core 52-64 may be single-mode with sufficient distance and cladding separating the cores such that the light in each core does not interact significantly with the light carried in other cores, Each core may include Fiber Bragg Gratings (FBGs) to provide strain measurements in one or more dimensions. Various systems and methods for monitoring the shape and relative position of optical fiber in three dimensions are described in U.S. patent application Ser. No. 11/180,389, filed Jul. 13, 2005, disclosing "Fiber optic position and shape sensing device and method relating thereto;" U.S. Provisional Pat. App. No. 60/588,336, filed on Jul. 16, 2004, disclosing "Fiber-optic shape and relative position sensing;" and U.S. Pat. No. 6,389,187, filed on Jun. 17, 1998, disclosing "Optical Fibre Bend Sensor," which are incorporated by reference herein in their entireties. In other alternatives, sensors employing other strain sensing techniques such as Rayleigh scattering, Ramaii scattering, Brillouin scattering, and Fluorescence scattering may be suitable.

In some embodiments, an array of FBG's is provided within each core. Each FBG comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBG's, the modulations are spaced by a known distance, thereby causing reflection of a known band of wavelengths. However, when a strain is induced on the fiber core, the spacing of the modulations will change, depending on the amount of strain in the core. Alternatively, backscatter or other optical phenomena that vary with bending of the optical fiber can be used to determine strain within each core.

Thus, to measure strain, light is sent down the fiber core, and characteristics of the returning light are measured. In this embodiment, the interrogator 12 generates and receives the returned light for each core. In alternative embodiments, more than one interrogator may be used. The FBG's produce a reflected wavelength that is a function of the strain on the fiber and its temperature. This FBG technology is commercially available from a variety of sources, such as Smart Fibres Ltd. of Bracknell, England. Use of FBG technology in position sensors for robotic surgery is described in U.S. Pat. No. 7,930,065, filed Jul. 20, 2006, disclosing "Robotic Surgery System Including Position Sensors Using Fiber Bragg Gratings," which is incorporated by reference herein in its entirety.

When applied to a multicore fiber, bending of the optical fiber induces strain on the cores that can be measured by monitoring the wavelength shifts in each core. By having two or more cores disposed off-axis in the fiber, bending of the fiber induces different strains on each of the cores. These strains are a function of the local degree of bending of the fiber. For example, regions of the cores containing FBG's, if located at points where the fiber is bent, can thereby be used to determine the amount of bending at those points. These data, combined with the known spacings of the FBG regions, can be used to reconstruct the shape of the fiber.

The sensor processing and control system 27 includes at least one processor (not shown), and typically a plurality of processors, for processing the information received front the interrogation system 27. The system 27 includes programmed instructions to implement some or all of the methods described herein. While system 27 is shown as a single block in the simplified schematic of FIG. 1, the system may comprise a number of data processing circuits with a portion of the processing optionally being performed in different locations. Any of a wide variety of centralized or distributed data processing architectures may be employed. Similarly, the programmed instructions may be implemented as a number of separate programs or subroutines, or they may be integrated into a number of other aspects of the robotic systems described herein.

Figure 3:
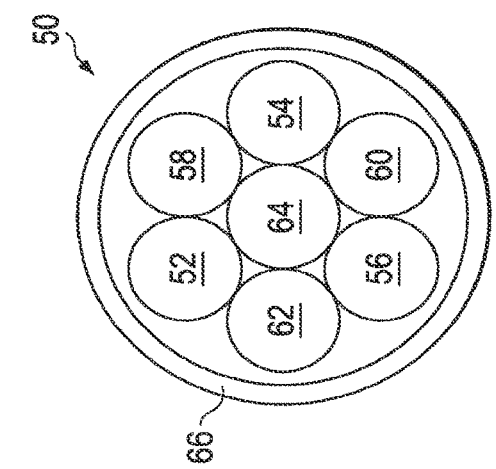
FIG. 3 is a cross-sectional view of the multi-core optical fiber component of FIG. 2.

In the embodiment of FIGS. 2 and 3, the central core 64 is centered within a radial array of the cores 52-64. The six cores 52-64 are arranged in two triads with cores 52, 54, 56 forming a first triad and cores 58, 60, 62 forming a second triad. The three optical cores in each triad are arranged in a triangular shape (in cross-section) and evenly spaced about a central axis A1 through the central core 64 at approximately 120° apart. The sensor device 16 can include a plurality of sections along its axial length, between proximal end 16a and distal end 16b, with strain values determined for each core at each axial section of the sensor device.

Figure 4:
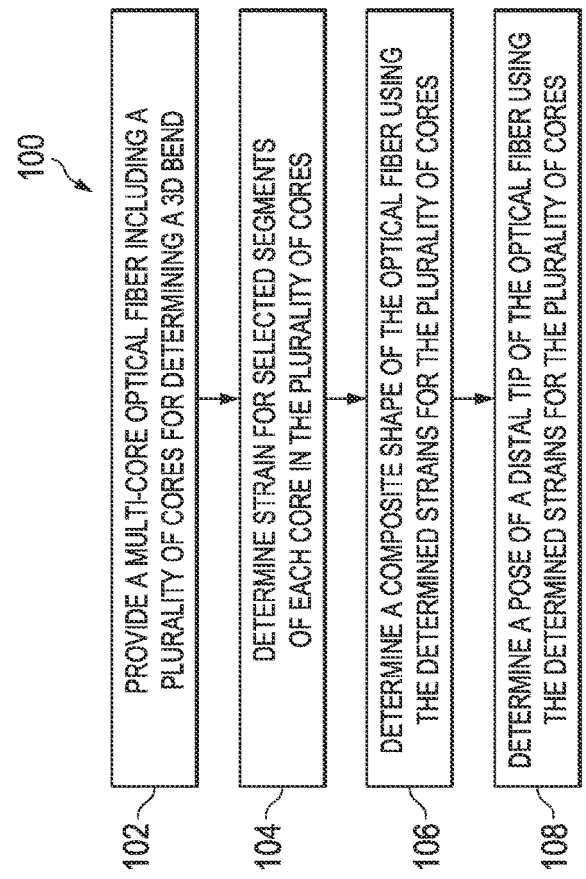
FIG. 4 illustrates a method of using a sensor system according to an embodiment of the present disclosure.
Figure 5:
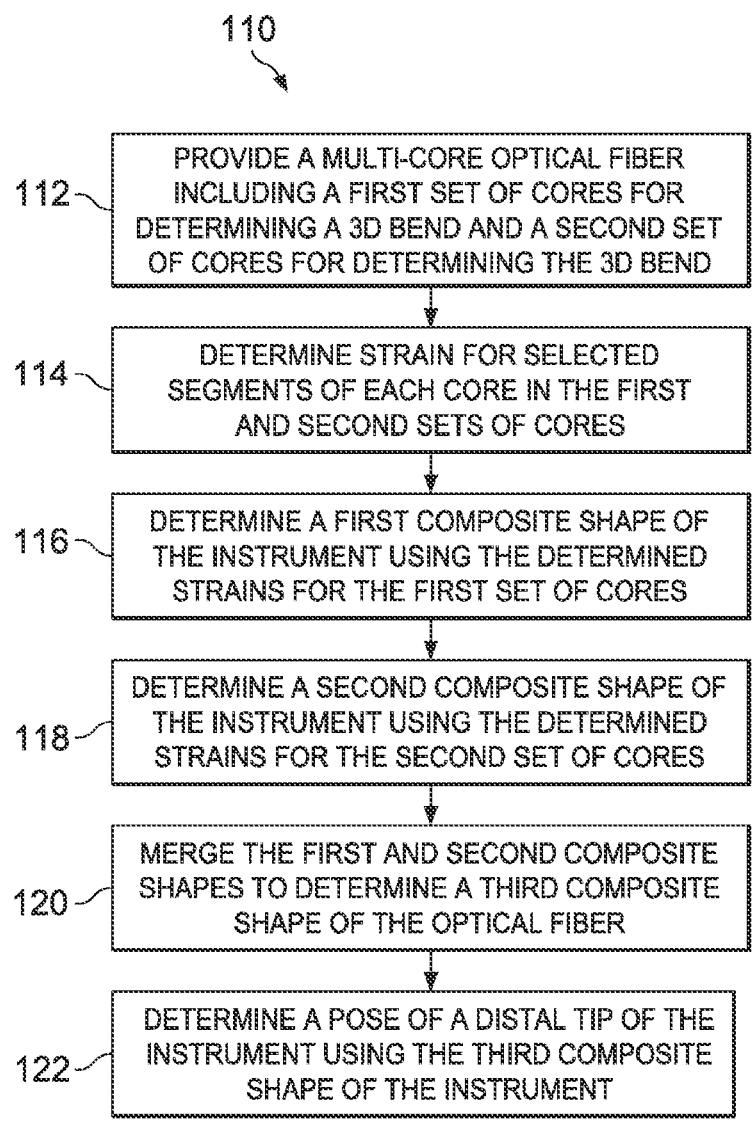
FIG. 5 illustrates a method of using a sensor system according to another embodiment of the present disclosure.

The strain values from at least three cores can be used to calculate the bend of the axial section. The bend values from each axial section may be combined to calculate the shape of the sensor device. From the shape of the sensor device, a position and orientation of the distal ends 16b, 18b, 20b or other axial portions of the sensor devices may be determined. FIGS. 4 and 5 provide alternative methods for determining the shape of a sensor device and thus, the pose of the distal end of the sensor device. Both of these methods use redundant optical fiber shape information to refine the accuracy of the final determined sensor shape.

In the embodiment of FIG. 4, a method 100 for determining the pose of a distal tip of a multi-core optical fiber (e.g., the distal end of the fiber in sensor devices 16, 18, 20) includes, at 102, providing the multi-core optical fiber which includes a plurality of cores (e.g., the six cores 52, 54, 56, 58, 60, 62) for determining a three-dimensional end of the fiber. Three cores are the minimum required to determine three-dimensional shape. The use of all six cores, radially arranged around the center core, provides redundant shape information that may be combined to generate a more accurate sensor shape. At 104, the method includes determining a strain for selected axial segments or all of the axial segments of each core in the plurality of cores.

At 106, the method includes determining a composite shape of the optical fiber using the determined strains for the plurality of cores. For example, the strains in all of the cores may be combined to reconstruct the bending, twisting, compression, and other shape characteristics that define the overall composite shape of the optical fiber. For example, with reference to FIG. 3, if the strains in cores 58 and 54 indicate compression (negative strain), the strains in 62, 56 indicate stretching (positive strain), and the strains in 52, 64, 60 are neutral, than the best fitting bend/twist angle would be a pure bend toward cores 54, 58 around a line passing through cores 52, 60.

At 108, the method includes determining a pose of a distal end of the optical fiber using the determined strains for the plurality of cores. For example, with a proximal end of the optical fiber held in a fixed pose (e.g., by the reference fixture 14), the determined composite shape of the optical fiber may be cumulatively applied to the proximal end fixed pose to determine the pose of intermediate portions along the axial length of the optical fiber. Using this method, the pose of the distal end of the optical fiber may be determined.

In the embodiment of FIG. 5, a method 110 for determining the pose of a distal tip of a multi-core optical fiber (e.g., the distal end of the fiber in sensor device 16, 18, 20) includes at 112, providing the multi-core optical fiber which includes a first set of cores (e.g., first triad 52, 54, 56) for determining a three-dimensional shape of the fiber and a second set of cores (e.g., second triad 58, 60, 62) for determining a three-dimensional shape of the fiber. A single triad of cores is the minimum required to determine three-dimensional shape. However, for measuring twist, each set of cores may include a fourth core, the central core 64, in addition to the three radially arranged cores. The use of two triads (or two triads plus the center core), provides redundant shape information that may be combined to generate a more accurate sensor shape. At 114, the method includes determining a strain for selected segments or all of the segments of each core in the first and second sets of cores.

At 116, the method includes determining a composite shape of the optical fiber using the determined strains for the first set of cores. For example, the shape of the optical fiber may be reconstructed from the bending, twisting, compression, and other shape characteristics derived from the three-dimensional strains of the first triad of cores that define the overall composite shape of the optical fiber. At 118, the method includes determining a composite shape of the optical fiber using the determined strains for the second set of cores. For example, the shape of the optical fiber may be reconstructed from the bending, twisting, compression, and other shape characteristics derived from the three-dimensional strains of the second triad of cores that define the overall composite shape of the optical fiber.

At 120, the method includes merging the first and second composite shapes to determine a third composite shape of the optical fiber. For example, the shape of the optical fiber determined from the first triad may be averaged together with the shape of the optical fiber determined from the second triad to determine the composite shape of the optical fiber. In alternative embodiments, the shape from each triad may be represented as a series of twist and bend angles, and merging of the two shapes may entail averaging those twist and bend angle sequences to reconstruct a composite shape based on the averaged sequences.

At 122, the method includes determining a pose of a distal end of the optical fiber using the determined strains for the first and second set of cores. For example, with a proximal end of the optical fiber held in a fixed pose (e.g., by the reference fixture 14), the composite shape of the optical fiber may be cumulatively applied to the proximal end fixed pose to determine the pose of intermediate portions along the axial length of the optical fiber. Using this method, the pose of the distal end of the optical fiber may be determined.

As described in die embodiments of FIGS. 6-13, multiple shape sensor devices may be constrained in a kinematic closed loop with certain portions coincident along the length of the sensor devices or with fixed kinematic relationships between one or more portions along the length of the sensor devices. The sensor devices may use a single traditional triad of optical cores for determining section bend and overall three dimensional shape or may use the above-described methods of using multiple triads of optical cores or the combined data from more than three optical cores to determine section bend and overall shape.

Redundant Sensor Device

Figure 6:
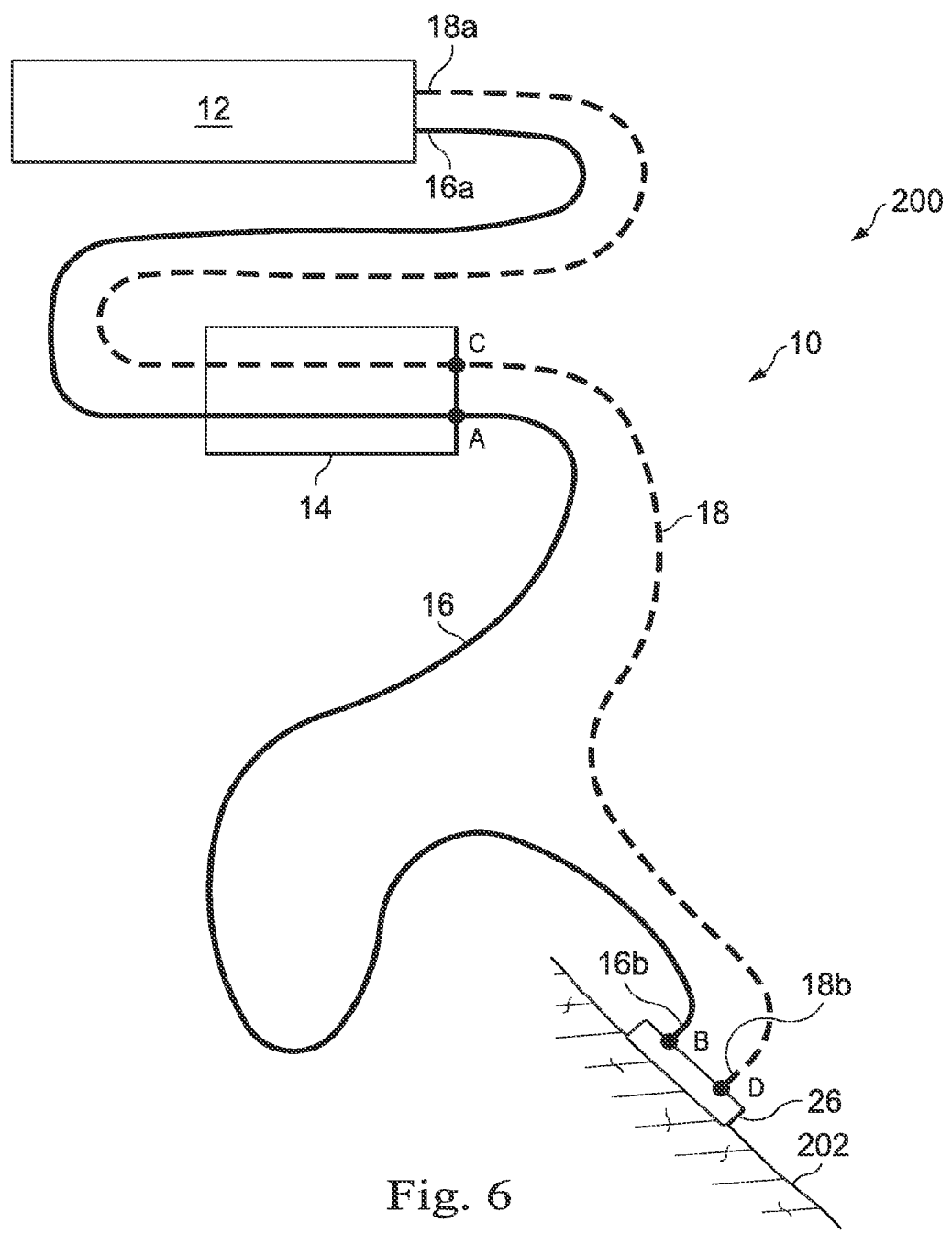
FIG. 6 is a sensor system with a plurality of optical fiber sensors in accordance with another embodiment of the present disclosure.

FIG. 6 illustrates a configuration 200 of the sensor system 10 in accordance with another embodiment of the present disclosure. In this embodiment, a two shape sensor devices 16, 18 are attached between a common reference fixture 14 and a common target. In this example, the target is an anatomic target 202 (e.g., a bone or soft tissue of the patient anatomy). In other embodiments, be common target of the sensor devices may be an interventional instrument or an implanted device. As will be described, the measured shapes of the sensor devices and their known kinematic relationships at one or more locations can be used to generate a more accurate position of the target structure.

In this configuration, the proximal ends 16*a*, 18*a* of sensor devices 16, 18 respectively, are connected to interrogation system 12. The sensor device 16 is held by the reference fixture 14 in a fixed kinematic pose at location A, and the sensor device 15 is held by the reference fixture 14 in a fixed kinematic pose at location C. At locations A and C, the three dimensional position offsets between the sensor devices and the three dimensional orientation offsets between the sensor devices are known. The distal end 16*b* of the sensor device 16 is coupled to the target fixture 26 at location B, and the distal end 18*b* of the sensor device 18 is coupled to the target fixture 26 at location D. The target fixture 26 holds the distal ends 16*b* and 18*b* in fixed kinematic poses with respect to the target fixture and with respect w each other. At locations B and D, the three dimensional position offsets between the sensor devices and the three dimensional orientation offsets between the sensor devices are known. The target fixture 26 is affixed to a target tissue 202 of the patient anatomy. As the target fixture 26 moves with the patient anatomy due to, for example, respiration, cardiac movement, patient ambulation, or tissue manipulation by a clinician during an interventional procedure, the sensor portions 16*b*, 18*b* are maintained in a fixed kinematic relationship with respect to each other.

In this embodiment, the length of the sensor device 16 between the locations A and 13 is different (in this embodiment longer) than the length of the sensor device 18 between locations C and D. The sensor devices 16, 18 may enter the patient anatomy anywhere along the length between AB and CD, respectively. For example, each sensor device may be coupled to the exterior anatomy of the patient or may extend within the free space surrounding the patient anatomy for the majority of the length between reference fixture and the target fixture and enter the patient anatomy just near the distal end of the sensor device where it is attached to the target fixture. The portion of the sensor devices between the reference fixtures and the target fixtures may be housed in a robust coating that protects the integrity of the optical fiber but allows for flexure and movement of the sensor device along the exterior patient anatomy or in the free space surrounding the patient anatomy. For example, a 3 mm diameter protective jacket may cover the sensor device outside of the patient anatomy. Alternatively, the sensor devices may enter the patient anatomy through natural or surgically created orifices and pass through natural or surgically created anatomical lumens to reach the target fixture and the target tissue.

Figure 7:
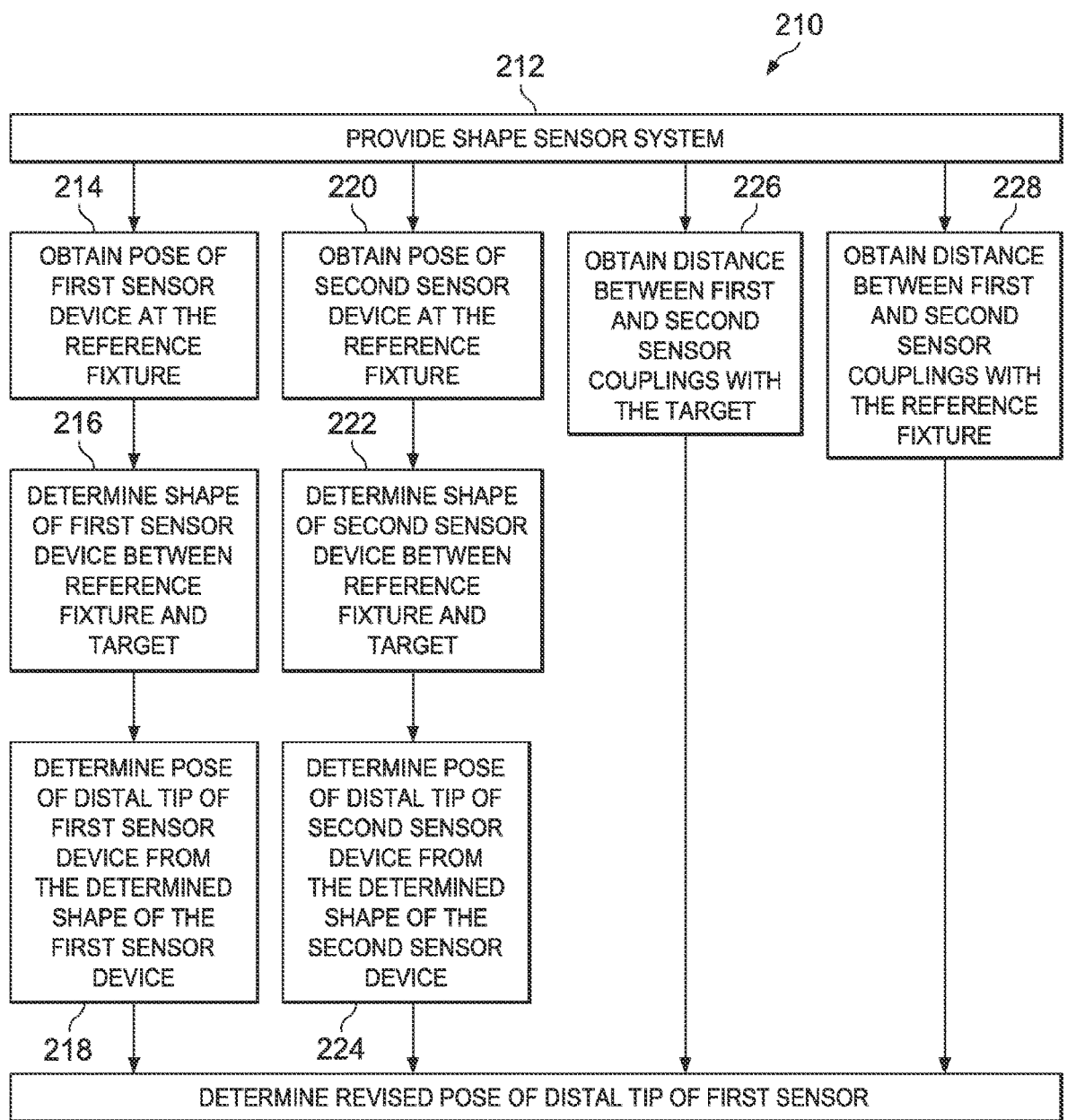
FIG. 7 illustrates a method of using the sensor system of FIG. 6.

FIG. 7 illustrates a method 210 of using the sensor system 10 as configured in FIG. 6. At 212, the sensor system 10 is provided as configured in FIG. 6 with the target fixture 26 attached to the target tissue 202. The target tissue 202 may be, for example, a bone such as a vertebral body or a portion of a hip joint. Alternatively, the target tissue 202 may be soft tissue such as an organ in the patient abdomen or a portion of the patient's brain. At 214, the method 210 includes obtaining the pose of the sensor device 16 at location A where it is fixed to the reference fixture 14. For example, obtaining the pose of the sensor device at location A may include knowing where the start is along the sensor device based on a calibration procedure and the fact that the sensor device is affixed to the reference fixture at location A. Alternatively, obtaining the pose of the sensor device at location A may include detecting a known feature (e.g., a 90° bend or a small bump) in the sensor device. The use of a known shape feature is described in further detail in U.S. patent application Ser. No. 12/617,995, filed on Nov. 13, 2009, disclosing "Method and System to Sense Relative Partial-Pose Information Using a Shape Sensor," which is incorporated by reference herein in its entirety. At 216, the sensor device 16 is interrogated to determine the shape of the sensor device between locations A and B. At 218, a pose of a distal end 16b of the sensor device 16 is obtained using the determined shape of the sensor device. For example, with the portion of the optical fiber held in a fixed pose at A by the reference fixture 14, the composite shape of the sensor device may be cumulatively applied to the fixed pose at A to determine the pose of intermediate portions along; the axial length of the sensor device between A and B. Using this method, the pose of the distal end 16b of the sensor device 16 may be determined.

At 220, the method 210 includes obtaining the pose of the sensor device 18 at location C where it is fixed to the reference fixture 14. At 222, the sensor device 18 is interrogated to determine the shape of the sensor device between locations C and D. At 224, a pose of a distal end 18b of the sensor device 18 is obtained using the determined shape of the sensor device. For example, with the portion of the optical fiber held in a fixed pose at C by the reference fixture 14, the composite shape of the sensor device may be cumulatively applied to the fixed pose at C to determine the pose of intermediate portions along the axial length of the sensor device between C and D. Using this method, the pose of the distal end 18b of the sensor device 18 may be determined.

At 226, the method 210 includes obtaining the three dimensional offset distance and/or orientation differences between the sensor devices 16, 18 at the target fixture 26 (i.e., B and D, respectively). At 228, the method includes obtaining the three dimensional offset distance and/or orientation difference between the sensor devices 16, 18 at the reference fixture 14 (i.e., at A and C, respectively).

At 230, the method 210 includes determining a revised pose for the distal end 16b of the shape sensor 16. For example, the pose of the distal end 18b of the sensor device 18 may be adjusted by the known offsets between the sensor devices at locations A and C and at locations B and D to generate a redundant determination or revised pose of the distal end 16b of the sensor device 16. Likewise, the distal end 16b may be adjusted by the known offsets between the sensor devices at locations A and C and at locations B and D to generate a redundant determination or revised pose of the distal end 18b of the sensor device 18. With this method, the position and orientation of the target may be determined with greater accuracy than would be possible using a single sensor device on its own.

Looped Sensor Device

Figure 8:
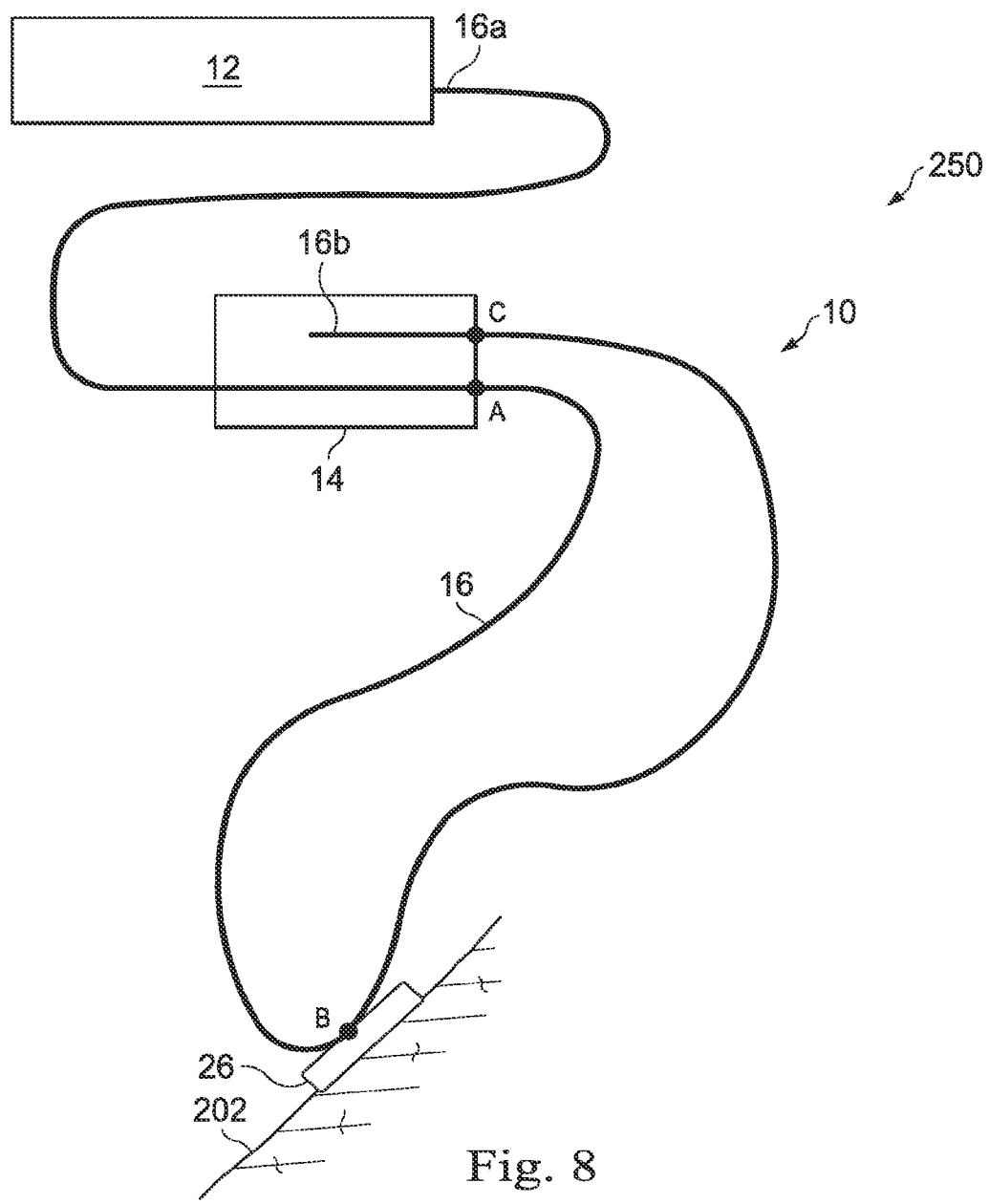
FIG. 8 is a sensor system with a single looped optical fiber sensor in accordance with another embodiment of the present disclosure.

FIG. 8 illustrates a configuration 250 of the sensor system 10 in accordance with another embodiment of the present disclosure. In this embodiment, a single sensor device is looped from a reference fixture, to a target, and back to the reference fixture. As will be described, the measured shapes of the sensor device sections between the reference fixture and the target and their known kinematic relationships at one or more locations can be used to generate a more accurate position of the target.

In this configuration, the proximal end 16a of sensor devices 16 is connected to interrogation system 12, The sensor device 16 is held by the reference fixture 14 in a fixed kinematic pose al location A. Another portion of e sensor device 16 is coupled to the target fixture 26 at location B. The distal end portion 16b of the sensor device 16 is coupled to the reference fixture 114 in a fixed kinematic pose at location C. Thus, the sensor device 16 forms a loop with known three dimensional position offsets of the sensor device portions between A and C and known three dimensional orientation offsets of the sensor device portions between A and C. The target fixture 26 holds an intermediate portion of the sensor device 16 in a fixed kinematic pose with respect to the target fixture. The target fixture 26 is affixed to a target tissue 202 of the patient anatomy. As the target fixture 26 moves with the patient anatomy, the sensor portion coupled to the target fixture 26 is maintained in a fixed kinematic relationship with respect to the target fixture. In this configuration, the sensor device section between A and B serves as a first shape sensor, and the sensor device section between C and B serves as a second shape sensor. The length of the sensor device 16 between the locations A and B may be different (in this embodiment shorter) than the length between locations C and B. The sensor device 16 may enter the patient anatomy anywhere along the length between AB and may exit the patient anatomy anywhere along the length between BC. For example, the sensor device may be coupled to the exterior anatomy of the patient or may extend within the free space surrounding the patient anatomy for the majority of the lengths between reference fixture and the target fixture and enter/exit the patient anatomy just near the portion of the sensor device that is attached to the target fixture. The portion of the sensor device between the reference fixture and the target fixture may be housed in a robust coating that protects the integrity of the optical fiber but allows for flexure and movement of the sensor device along the exterior patient anatomy or in the free space surrounding the patient anatomy. Alternatively, the sensor device may enter the patient anatomy through natural or surgically created orifices and pass through natural or surgically created anatomical lumens to reach the target fixture and the target tissue.

In the embodiment of FIG. 8, the looped sensor device 16 may be coupled to the target fixture such that the optical fiber(s) of the sensor device are curved smoothly, without kinking, excessive twisting, excessive bending, or other arrangements that induce high strain or damage to the fiber. For example, the target fixture 26 may be constructed with a preformed groove sized to receive the shape sensor 16 and hold it in a predetermined curved shape, thus resisting kinking or excessive twisting at the target fixture.

Figure 9:
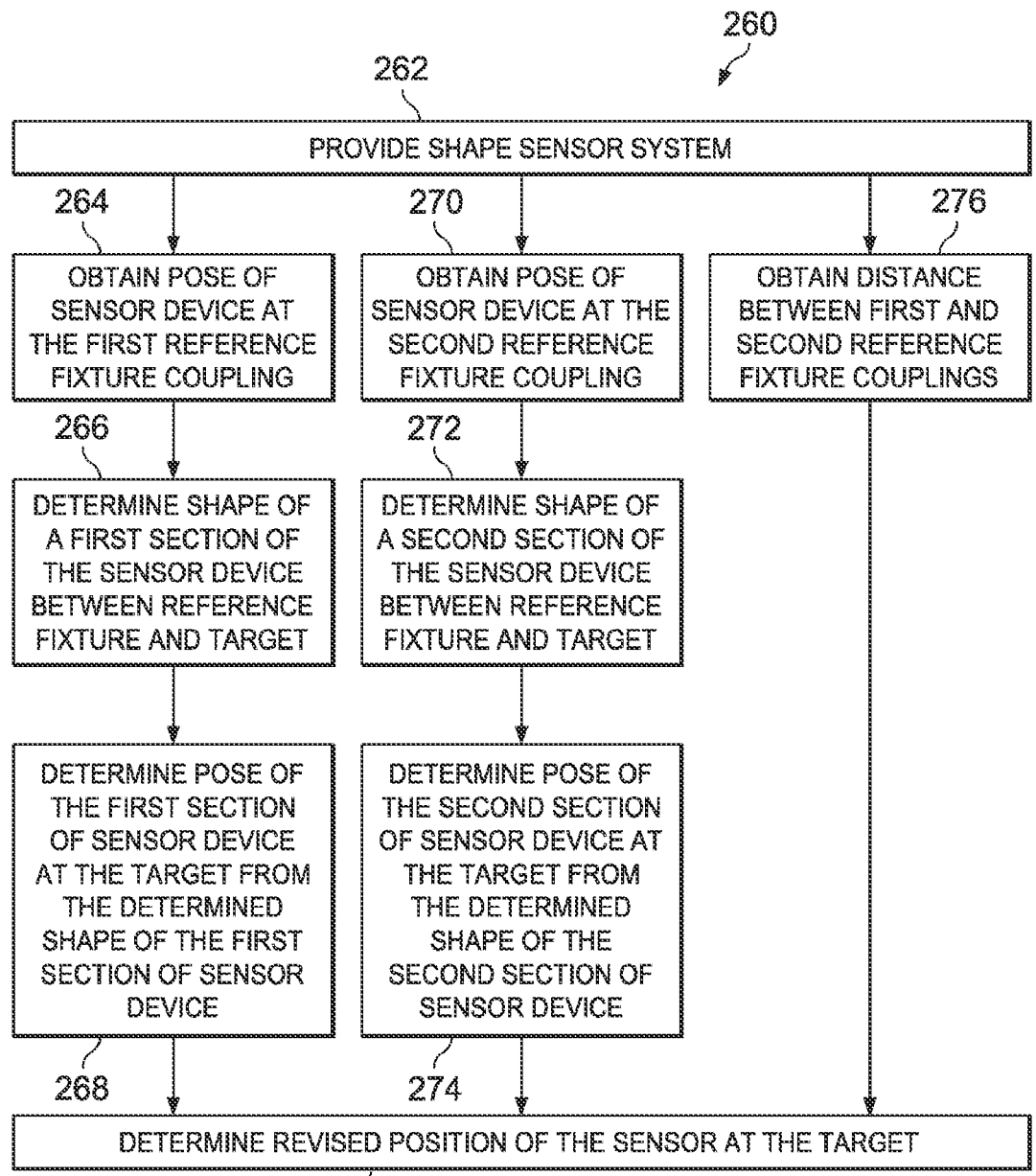
FIG. 9 illustrates a method of using the sensor system of FIG. 8.

FIG. 9 illustrates a method 260 of using the sensor system 10 as configured in FIG. 8. At 262, the sensor system 10 is provided as configured in FIG. 8 with the target fixture attached to the target tissue 202. At 264, the method 260 includes obtaining; the pose of the sensor device 16 at location A where it is fixed to the reference fixture 14. At 266, the sensor device 16 is interrogated to determine the shape of a first section of the sensor device between locations A and B. At 268, a pose of the portion of the sensor device 16 coupled to the target fixture at B is obtained using the determined shape of the first section of the sensor device between locations A and B. For example, with the portion of the optical fiber held in a fixed pose at A by the reference fixture 14, the composite shape of the first section of the sensor device may be cumulatively applied to the fixed pose at A to determine the pose of intermediate portions along the axial length of the sensor device between A and B. Using this method, the pose of the first section of the sensor device at location B may be determined.

At 270, the method 260 includes obtaining, the pose of the sensor device 16 at location C where it is fixed to the reference fixture 14. At 272, the sensor device 16 is interrogated to determine the shape of a second section of the sensor device between locations C and B. At 274, a pose of the portion of the sensor device 16 coupled to the target fixture at B is obtained using the determined shape of the second section of the sensor device between C and B. For example, with the portion of the optical fiber held in a fixed pose at C by the reference fixture 14, the composite shape of the second section of the sensor device may be cumulatively applied to the fixed pose at C to determine the pose of intermediate portions along the axial length of the sensor device between C and B. Using this method, the pose of the second section of the sensor device at location B may be determined.

At 276, the method 260 includes determining the sensor device pose at the target based on the first section (A-B) pose at B and on the second section (C-B) pose at B. For example, the determination of the sensor device pose at the target may be determined by averaging the first and second section poses at B (with correct origination poses at A and C assumed). With this method, the position and orientation of the target at B may be determined with greater accuracy than may be possible using a single sensor device between the reference fixture and the target.

FIG. 10 again illustrates the configuration 250 of the sensor system 10. In this configuration, the shape sensor 16 is coupled to the reference fixture 14 at A, to the target fixture 26 at B, and to the reference fixture 14 at C, as previously described. This embodiment provides error correction and redundancy for determining the pose of the sensor at B by using a measured shape 252 of the sensor device 16, between locations A and C'. The measured shape 252 of the third shape sensor section between A and C' may be slightly different than the real shape of the third shape sensor section between A and C. Measuring a multidimensional correction factor between real location C and the measured location C' provides information for correcting the accumulated error generated in the sensor device 16. This information may be used to reduce error in determining the position of location B'.

Figure 10:
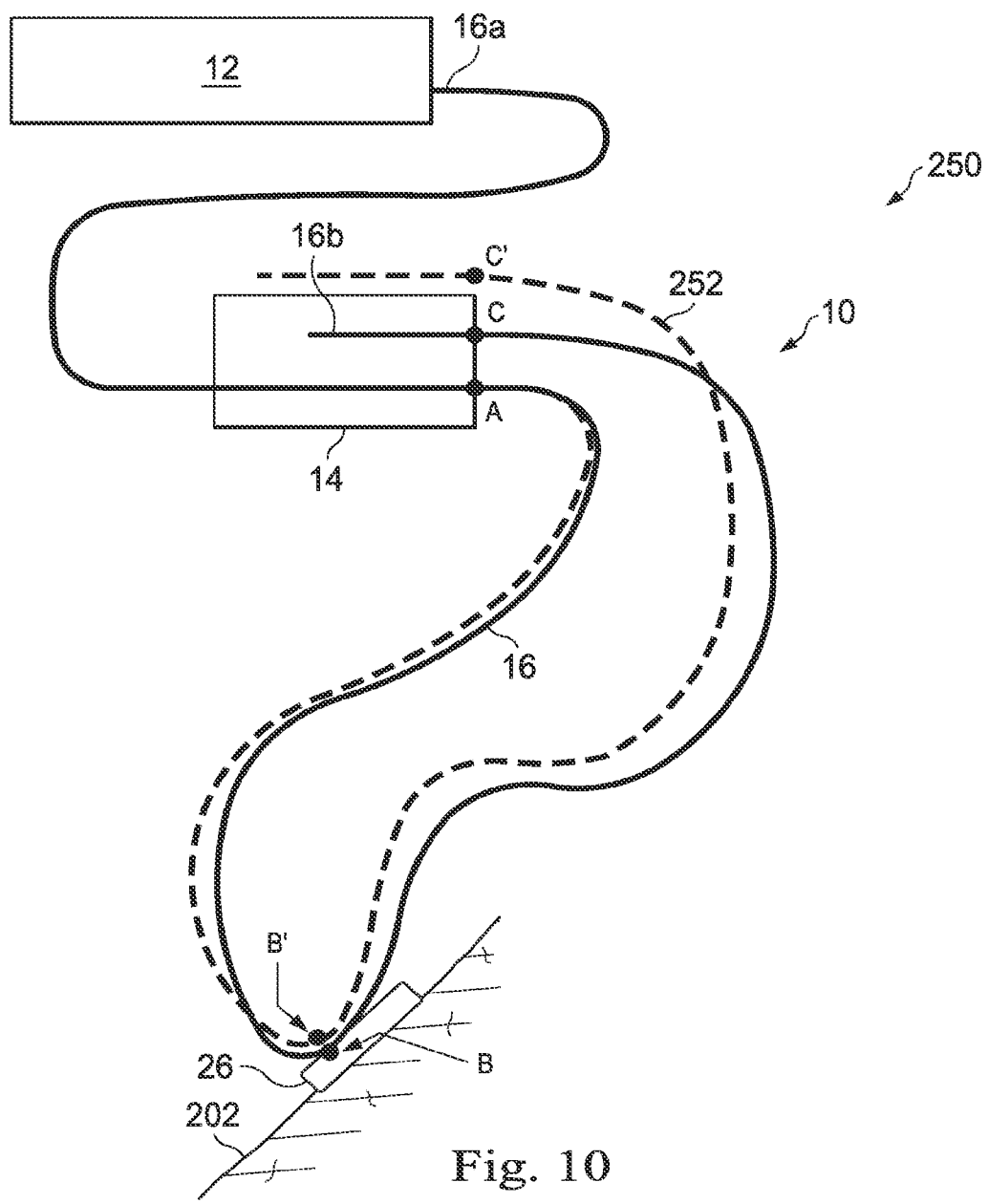
FIGS. 10 and 11 illustrate another method of using the sensor system of FIG. 10.
Figure 11:
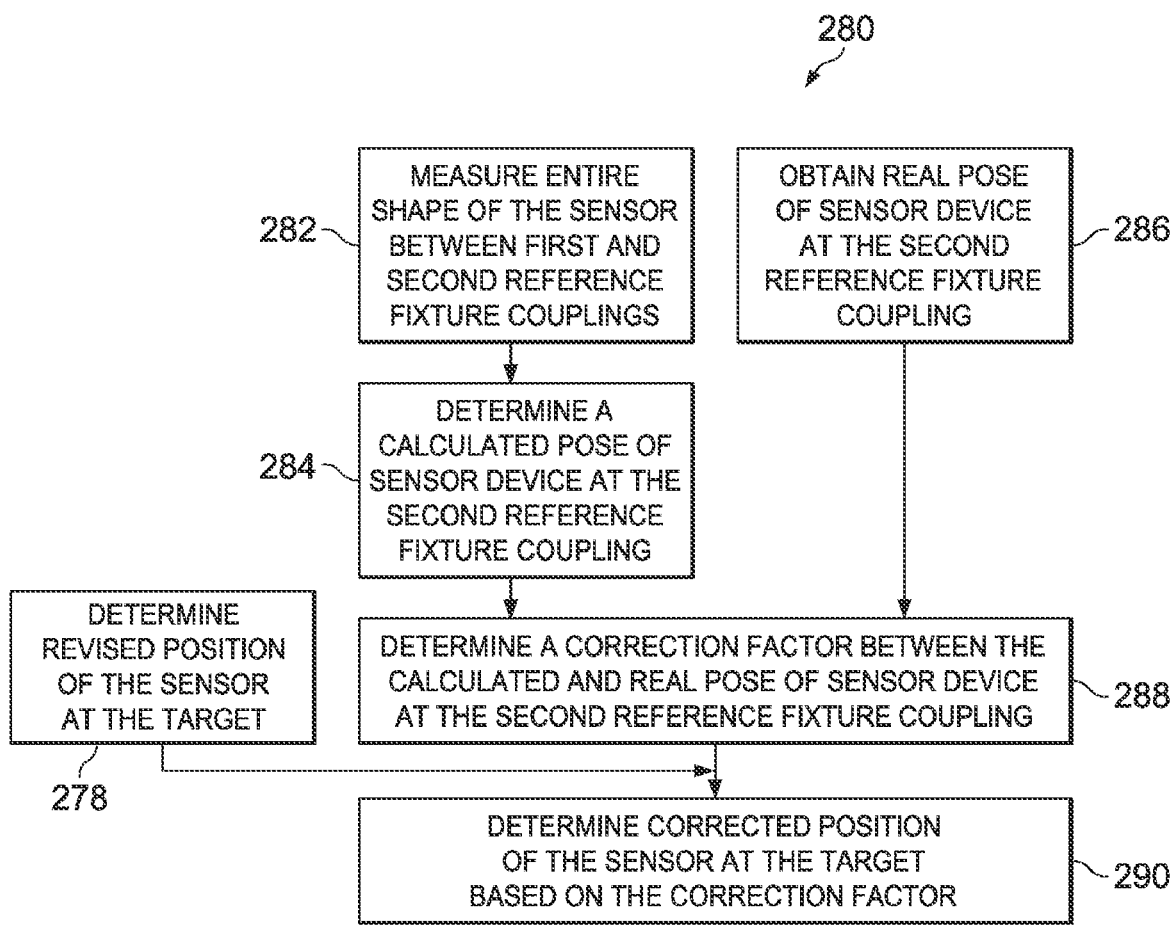

FIG. 11 illustrates a method 280 of using the sensor system 10 as configured in FIG. 10 to correct the position and orientation of the target at B. At 282, the sensor device 16 between A and C is interrogated to determine the measured shape 252 of the sensor device between A and C'. At 284, the pose of the sensor device 16 at B' and C' is obtained using the determined shape of the sensor device. For example, with the portion of the optical fiber held in a fixed pose at A by the reference fixture 14, the composite shape of the sensor device may be cumulatively applied to the fixed pose at A to measure the pose of intermediate portions along the axial length of the sensor device, including al B' and C'. At 286, the known real pose of the sensor device 16 at C, where it is fixed to the reference fixture 14, is obtained. At 288, a three dimensional first correction factor is calculated between the real pose of the sensor device at C and the calculated pose of the sensor device at C'. At 289, a three dimensional second correction factor is determined to correct the calculated pose of the target at B', based upon the first correction factor. For example, if the first correction factor is 2 cm in one direction, the second correction factor may be half (i.e., 1 cm) in the same direction. In other alternatives, the second correction factor may be greater or less than half of the first correction factor. Using the second correction factor, the measured position B' may be further corrected at 290 to determine an improved approximation of the pose of the sensor device 16 at the target location B. The corrected position B is determined by adjusting the position B' by the three dimensional second correction factor. With this method, the position and orientation of the looped sensor device at B may be determined with greater accuracy than may be possible using a single non-looped sensor device.

Redundant Sensor and interventional Instrument

FIG. 12 illustrates a configuration 310 of the sensor system 10 in accordance with another embodiment of the present disclosure. In this embodiment, three shape devices are attached to a common reference fixture, extend to different tools or anatomical locations, and join again at a common target. As will be described, the measured shapes of the sensor devices and their known kinematic relationships at one or more locations can be used to generate a more accurate position of the target structure. In this configuration, the proximal ends 16a, 18a, 20a of sensor devices 16, 18, 20 respectively, are connected to the interrogation system 12. The sensor device 16 is held by the reference fixture 14 in a fixed kinematic pose at location A, the sensor device 18 is held by the reference fixture 14 in a fixed kinematic pose at location E, and the sensor device 20 is held by the reference fixture 14 in a fixed kinematic pose at location F. At locations A and E, the position offsets of the sensor devices 16, 18 between A and E and the orientation offsets of the sensor devices between A and E are known. At locations A and F, the three dimensional position offsets of the sensor devices 16, 20 between A and F and the three dimensional orientation offsets of the sensor devices between A and F are known. At locations F and F, the three dimensional position offsets of the sensor devices 18, 20 between E and F and the three dimensional orientation offsets of the sensor devices between F and F are known. The distal end 16b of the sensor device 16 is coupled to a target fixture 26a at location C, and an intermediate portion of the sensor device 16 (located along the axial length of the sensor device between the reference fixture 14 and the distal end 16b) is coupled to a target fixture 26a at location B. The distal end 18b of the sensor device 18 is coupled to the target fixture 26b at location D. The target fixture 26b holds the distal ends 16b and 18b in fixed kinematic poses with respect to the target fixture 26b and with respect to each other. At locations C and D, the position offsets of the sensor devices between C and D and the orientation offsets of the sensor devices between C and D are known. The target fixtures 26a is affixed to a target tissue 204 of the patient anatomy and the target fixture 26b is affixed to the target tissue 202 of the patient anatomy. As the target fixture 26b moves with the patient anatomy, the sensor distal end portions 16b, 18b are maintained in a fixed kinematic relationship with respect to each other. As the target fixture 26a moves with the patient anatomy, the intermediate portion of sensor device 16 maintains a fixed kinematic relationship with the target fixture 26a. The length of the sensor device 16 between the locations A and C may be different (in this embodiment longer) than the length of the sensor device 18 between locations E and D. The sensor devices 16, 18 may enter the patient anatomy anywhere along the length between AB and ED, respectively. The sensor device 16 between BC may emerge from the patient anatomy and reenter the patient anatomy. Alternatively, the sensor device 16 between BC may pass through a natural or surgically created passageway in the patient anatomy. In this embodiment, the distal end 20b of the sensor device 20 is affixed to the interventional instrument 22 and is maintained in a fixed kinematic relationship with respect to the interventional instrument.

In one example, the target tissues 202, 204 may be bones in the patient anatomy and the sensor devices may be attached to the target tissues to determine relative positions and relative motions of the bones. The sensor devices may be affixed to the bones by target fixtures that include hone screws, adhesives, or other known coupling systems.

The sensor devices 16, 18, 20 may include a single fiber or multiple fibers arranged in parallel. Alternatively, a sensor device may have serially connected fiber segments (i.e., "daisy-chained" segments) connected by optical couplers that permit interrogation across the connection. Thus, one segment would extend, for example, between locations A, B and that segment would be connected to another segment extending between locations B, C.

FIG. 13 illustrates a method 320 of using the sensor system 10 as configured in FIG. 12. At 322, the sensor system 12 is provided as configured in FIG. 12 with the target fixture 26a attached to the target tissue 204 and the target fixture 26b attached to the target tissue 202. At 324, the method 320 includes obtaining the pose of the sensor device 16 at location A where it is fixed to the reference fixture 14. At 326, the sensor device 16 is interrogated to determine the shape of the first section of the sensor device between locations A and B. At 328, a pose of the sensor device 16 at location B is obtained using the determined shape of the first section sensor device. For example, with the portion of the sensor device held in a fixed pose at A by the reference fixture 14, the composite shape of the first section of the sensor device may be cumulatively applied to the fixed pose at A to determine the pose of intermediate portions along the axial length of the sensor device between A and B. Using this method, the pose of the sensor device at location B may be determined. At 330, the method includes determining the shape of the sensor device 16 between the reference fixture 14 at location A and the target fixture 26b at location C. At 332, the pose of the distal end. 16b of the sensor device 16 at location C is determined from the shape of the sensor device 16 between A and C. With this method, the sensor devices 16, 18 form a kinematic loop that may be used to improve the determination of the locations of both target tissues 202, 204.

At 334, the method 320 includes obtaining the pose of the sensor device 18 at location E where it is fixed to the reference fixture 14. At 336, the sensor device 18 is interrogated to determine the shape of the sensor device between locations E and D. At 338, a pose of a distal end 18b of the sensor device 18 is obtained using the determined shape of the sensor device. For example, with the portion of the optical fiber held in a fixed pose at E by the reference fixture 14, the composite shape of the sensor device may be cumulatively applied to the fixed pose at E to determine the pose of intermediate portions along the axial length of the sensor device between E and D. Using this method, the pose of the distal end 18b of the sensor device 18 may be determined.

At 340, the method 210 includes obtaining the three dimensional offset distance and/or orientation difference between the sensor devices 16, 18 at the reference fixture 14 (i.e., at A and E, respectively). At 342, the three dimensional offset distance and/or orientation difference between the sensor devices 16, 18 at the target fixture 26b, i.e. at C and D, respectively, are obtained. At 344, the three dimensional offset distance and/or orientation difference between the sensor devices 16, 20 at the reference fixture 14 (i.e., at A and F, respectively) are obtained. At 346, the three dimensional offset distance and/or orientation difference between the sensor devices 18, 20 at the reference fixture 14 (i.e., at F and F, respectively) are obtained.

At 348, the method 320 includes obtaining the pose of the sensor device 20 at location. F where it is fixed to the reference fixture 14. At 350, the sensor device 20 is interrogated to determine the shape of the sensor device between locations F and G. At 352, a pose of a distal end 20b of the sensor device 20 is obtained using the determined shape of the sensor device. For example, with the portion of the optical fiber held in a fixed pose at F by the reference fixture 14, the composite shape of the sensor device 20 may be cumulatively applied to the fixed pose at F to determine the pose of intermediate portions along the axial length of the sensor device between F and G. Using this method, the pose of the distal end 20b of the sensor device 20 may be determined. The distal end 20 of the sensor device 20 may be fixed at a distal end of the interventional instrument 22 as shown in FIG. 1. Alternatively, the distal end 20 of the sensor device 20 may be fixed at a proximal end of the interventional instrument 22 as shown in FIG. 12. In various other configurations, the distal end 20 of the sensor device 20 may be fixed at other points on the interventional instrument that a clinician may have an interest in tracking.

At 354, the method 320 includes determining a revised pose for the distal end 16b of the shape sensor 16. For example, the pose of the distal end 18b of the sensor device 18 may adjusted based on the known offsets between locations A,E and the offsets between locations C,D to generate a redundant determination or revised pose of the distal end 16b of the sensor device 16. With this method, the position and orientation of the distal end 16b of the sensor device 16 may be determined with greater accuracy than would be possible using the single sensor device 16 on its own. At 356, the revised pose of the distal end 16b is tracked relative to the distal end 20b of the sensor device 20 carried by the interventional instrument 22.

The distal end 20b of the sensor 20 (or a portion of the interventional instrument 22 fixed with respect to the distal end 20b of the sensor 20) may be used to provide redundancy for refining the position of the distal end 16b of the sensor 16, For example, if the distal end 20b of the sensor is held at the target reference fixture (coincident with or in a known kinematic relationship with the distal end 16b) while the sensor device 20 is interrogated, the resulting shape of the sensor 20 may be used to determine the position of the distal end 20b at the target. Thus, the position of the distal end 20b and the known three dimensional offsets between the sensors at the reference fixture and the target fixture may be used to refine the pose of the distal end 16b using a method similar to that used for redundant sensor device 18.

Any of the described sensor system configurations may be used to assist in medical interventional procedures, including computer assisted systems. Computer assisted systems may include teleoperated interventional systems such as robotic interventional systems. Referring to FIG. 14 of the drawings, a teleoperated interventional system for use in, for example, surgical, diagnostic, therapeutic, or biopsy procedures, is generally indicated by the reference numeral 400. As shown in FIG. 1, the teleoperated interventional system 400 generally includes a robotic assembly 402 mounted to or near an operating table O on which a patient P is positioned. An interventional instrument system 404 is operably coupled to the robotic assembly 402. An operator input system 406 allows a surgeon S to view the surgical site and to control the operation of the interventional instrument system 404.

The operator input system 406 may be located at a surgeon's console which is usually located in the same room as operating table O. However, it should be understood that the surgeon S can be located in a different room or a completely different building from the patient P. Operator input system 406 generally includes one or more control device(s) for controlling the interventional instrument system 404. The control devices) may include any number of a variety of input devices, such as hand grips, joysticks, trackballs, data gloves, trigger-guns, hand-operated controllers, voice recognition devices, touch screens, body motion or presence sensors, or the like. In some embodiments, the control device(s) will be provided with the same degrees of freedom as the interventional instruments of the robotic assembly to provide the surgeon with telepresence, or the perception that the control device(s) are integral with the instruments so that the surgeon has a strong sense of directly controlling instruments. In other embodiments, the control device(s) may have more or fewer degrees of freedom than the associated interventional instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, or the like).

The robotic assembly 402 supports the interventional instrument system 404 and may comprise a kinematic structure of one or more non-servo controlled links (e.g., one or more links that may be manually positioned and locked in place, generally referred to as a set-up structure) and a robotic manipulator. The robotic assembly 402 includes plurality of actuators (e.g., motors) that drive inputs on the interventional instrument 404. These motors actively move in response to commands from the control system (e.g., control system 412). The motors include drive systems which when coupled to the interventional instrument 404 may advance the interventional instrument into a naturally or surgically created anatomical orifice and/or may move the distal end of the interventional instrument in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the motors can be used to actuate an articulable end effector of the instrument for grasping tissue in the jaws of a biopsy device or the like.

The robotic interventional system 400 also includes a sensor system 408 with one or more sub-systems for receiving information about the instruments of the robotic assembly. The sensor system 408 may include, for example, the shape sensor device 10 in any of the configurations described above. The sensor sub-systems may also include an electromagnetic (EM) position sensor system) and/or a visualization system for capturing images from the distal end of the catheter system.

The robotic interventional system 400 also includes a display system 410 for displaying an image of the surgical site and interventional instruments 404 generated by sub-systems of the sensor system 408. The display 410 and the operator input system 406 may be oriented so the operator can control the interventional instrument system 404 and the operator input system 406 as if viewing the workspace in substantially true presence. True presence means that the displayed tissue image appears to an operator as if the operator was physically present at the image location and directly viewing the tissue from the perspective of the image.

Alternatively or additionally, display system 410 may present images of the surgical site recorded and/or modeled preoperatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. The presented preoperative images may include two-dimensional, three-dimensional, or four-dimensional (including time based or velocity based information) images and models.

In some embodiments, the display system 410 may display a virtual visualization image in which the actual location of the interventional installment is registered (e.g., dynamically referenced) with preoperative or concurrent images to present the surgeon with a virtual image of the internal surgical site at the location of the tip of the surgical instrument.

In other embodiments, the display system 410 may display a virtual visualization image in which the actual location of the interventional instrument is registered with prior images (including preoperatively recorded images) or concurrent images to present the surgeon with a virtual image of an interventional instrument at the surgical site. An image of a portion of the interventional instrument 404 may be superimposed on the virtual image to assist the surgeon controlling the interventional instrument.

The robotic interventional system 400 also includes a control system 412. The control system 412 includes at least one processor (not shown), and typically a plurality of processors, for effecting control between the interventional instrument system 404, the operator input system 406, the sensor system 408, and the display system 410. The control system 412 may include common computer components including a logic unit, such as an arithmetic or logical adder, and one or more memory devices. The control system 412 also includes programmed instructions (e.g., a computer-readable medium storing the instructions) to implement some or all of the methods described herein.

While control system 412 is shown as a single block in the simplified schematic of FIG. 1, the system may comprise a number of data processing circuits with a portion of the processing optionally being performed on or adjacent the robotic assembly 402, a portion being performed at the operator input system 406, and the like. The control system 24 and the sensor processing and control system 27 may be components of the control system. Any of a wide variety of centralized or distributed data processing architectures may be employed. Similarly, the programmed instructions may be implemented as a number of separate programs or subroutines, or they may be integrated into a number of other aspects of the robotic systems described herein. In one embodiment, control system 412 supports wireless communication protocols such as Bluetooth, IrDA, HomeRF, IEEE 802.11, DECT, and Wireless Telemetry.

In some embodiments, control system 412 may include one or more servo controllers to provide force and torque feedback from the interventional instrument system 404 to one or more corresponding servomotors for the operator input system 406. The servo controller(s) may also transmit signals instructing robotic assembly 402 to move the interventional instruments 404 which extend into an internal surgical site within the patient body via openings in the body. Any suitable conventional or specialized servo controller may be used. A servo controller may be separate from, or integrated with, robotic assembly 402. In some embodiments, the servo controller and robotic assembly are provided as part of a robotic arm cart positioned adjacent to the patient's body.

The control system 412 may further include a virtual visualization system to provide navigation assistance to the interventional instruments 404. Virtual navigation using the virtual visualization system is based upon reference to an acquired dataset associated with the three dimensional structure of the anatomical passageways. More specifically, the virtual visualization system processes images of the surgical site recorded and/or modeled using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software is used to convert the recorded images into a two dimensional or three dimensional model of a partial or an entire anatomical organ or anatomical region. The model describes the various locations and shapes of the passageways and their connectivity. The images used to generate the model may be recorded preoperatively or intra-operatively during a clinical procedure. In an alternative embodiment, a virtual visualization system may use standard models (i.e., not patient specific) or hybrids of a standard model and patient specific data. The model and any virtual images generated by the model may represent the static posture of a deformable anatomic region during one or more phases of motion (e.g., during an inspiration/expiration cycle of a lung) or during induced anatomic motion (e.g., patient repositioning or instrument-caused deformation).

During a virtual navigation procedure, the sensor system 408 may be used to compute an approximate location of the instrument with respect to the patient anatomy. The location can be used to produce both macro-level tracking images of the patient anatomy and virtual internal images of the patient anatomy. Various systems for using fiber optic sensors to register and display an interventional implement together with preoperatively recorded surgical images, such as those from a virtual visualization system, are known. For example U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety, discloses one such system.

The robotic interventional system 400 may further include optional operation and support systems (not shown) such as illumination systems, steering control systems, irrigation systems, and/or suction systems. In alternative embodiments, the robotic system may include more than one robotic assembly and/or more than one operator input system. The exact number of manipulator assemblies will depend on the surgical procedure and the space constraints within the operating room, among other factors. The operator input systems may be collocated, or they may be positioned in separate locations, Multiple operator input systems allow more than one operator to control one or more manipulator assemblies in various combinations.

One or more elements in embodiments of the invention may be implemented in software to execute on a processor of a computer system such as control system 412. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, intranet, etc.

Note that the processes and displays presented may not inherently be related to any particular computer or other apparatus. The required structure for a variety of these systems ill appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:
1. A method, comprising:
receiving shape data from a first plurality of optical cores of an elongated optical fiber, the elongated optical fiber including a plurality of sections, the first plurality of optical cores extending at least within a first section of the plurality of sections;
determining a first shape of the elongated optical fiber at least within the first section based on the shape data from the first plurality of optical cores;
receiving shape data from a second plurality of optical cores extending at least within the first section of the plurality of sections of the elongated optical fiber;
determining a second shape of the elongated optical fiber at least within the first section based on the shape data from the second plurality of optical cores;

determining a third shape of the elongated optical fiber at least within the first section by combining the first shape of the elongated optical fiber at least within the first section and the second shape of the elongated optical fiber at least within the first section; and tracking a position of an instrument within a patient anatomy based on the third shape of the elongated optical fiber, the elongated optical fiber at least partially extending within the instrument.

2. The method of claim 1 wherein the shape data measured from the first plurality of optical cores includes three dimensional shape data, and wherein the shape data measured from the second plurality of optical cores includes three dimensional shape data.

3. The method of claim 1 wherein the first and second plurality of optical cores each include at least three optical cores.

4. The method of claim 1 wherein determining the third shape of the elongated optical fiber at least within the first section comprises averaging the first and second shapes of the elongated optical fiber to generate the third shape of the elongated optical fiber at least within the first section.

5. The method of claim 1 wherein determining the first shape of the elongated optical fiber at least within the first section comprises combining shape data from each optical core of the first plurality of optical cores to generate the first shape of the elongated optical fiber at least within the first section, and wherein determining the second shape of the elongated optical fiber at least within the first section comprises combining shape data from each optical core of the second plurality of optical cores to generate the second shape of the elongated optical fiber at least within the first section.

6. The method of claim 1 wherein the shape data from the first plurality of optical cores is a composite shape of the first plurality of optical cores, and wherein the shape data from the second plurality of optical cores is a composite shape of the second plurality of optical cores.

7. The method of claim 1 wherein the first plurality of optical cores extends in a longitudinal direction of the elongated optical fiber.

8. The method of claim 7 wherein a second section of the plurality of sections of the elongated optical fiber is in a different position from the first section in the longitudinal direction.

9. The method of claim 1 wherein the first plurality of optical cores includes a central core extending along a central axis of the first plurality of optical cores, and wherein the second plurality of optical cores includes the central core extending along a central axis of the second plurality of optical cores.

10. The method of claim 9 wherein the shape data from the first plurality of optical cores includes first twist data received from the central core, and wherein the shape data from the second plurality of optical cores includes second twist data received from the central core.

11. A system comprising:
a processor; and
a memory including computer readable instructions stored thereon, the computer readable instructions, when executed by the processor, cause the system to:
receive shape data from a first plurality of optical cores of an elongated optical fiber, the elongated optical fiber including a plurality of sections, the first plurality of optical cores extending at least within a first section of the plurality of sections;

determine a first shape of the elongated optical fiber at least within the first section based on the shape data from the first plurality of optical cores;

receive shape data from a second plurality of optical cores extending at least within the first section of the plurality of sections of the elongated optical fiber;

determine a second shape of the elongated optical fiber at least within the first section based on the shape data from the second plurality of optical cores;

determine a third shape of the elongated optical fiber at least within the first section by combining the first shape of the elongated optical fiber at least within the first section and the second shape of the elongated optical fiber at least within the first section; and track a position of an instrument within a patient anatomy based on the third shape of the elongated optical fiber, wherein the elongated optical fiber is at least partially extending within the instrument.

12. The system of claim 11 wherein determining the third shape of the elongated optical fiber at least within the first section comprises averaging the first and second shapes of the elongated optical fiber to generate the third shape of the elongated optical fiber at least within the first section.

13. The system of claim 11 wherein determining the first shape of the elongated optical fiber at least within the first section comprises combining shape data from each optical core of the first plurality of optical cores to generate the first shape of the elongated optical fiber at least within the first section, and wherein determining the second shape of the elongated optical fiber at least within the first section comprises combining shape data from each optical core of the second plurality of optical cores to generate the second shape of the elongated optical fiber at least within the first section.

14. The system of claim 11 wherein the shape data from the first plurality of optical cores is a composite shape of the first plurality of optical cores, and wherein the shape data from the second plurality of optical cores is a composite shape of the second plurality of optical cores.

15. The system of claim 11 wherein the shape data measured from the first plurality of optical cores includes three dimensional shape data, and wherein the shape data measured from the second plurality of optical cores includes three dimensional shape data.

16. The system of claim 15 wherein the first and second plurality of optical cores each include at least three optical cores.

17. The system of claim 11 wherein the first plurality of optical cores extends in a longitudinal direction of the elongated optical fiber.

18. The system of claim 17 wherein a second section of the plurality of sections of the elongated optical fiber is in a different position from the first section in the longitudinal direction.

19. The system of claim 11 wherein the first plurality of optical cores includes a central core extending along a central axis of the first plurality of optical cores, and wherein the second plurality of optical cores includes the central core extending along a central axis of the second plurality of optical cores.

20. The system of claim 19 wherein the shape data from the first plurality of optical cores includes first twist data received from the central core, and wherein the shape data from the second plurality of optical cores includes second twist data received from the central core.

* * * * *